(12) United States Patent
Bhattacharya et al.

(10) Patent No.: US 7,534,882 B2
(45) Date of Patent: May 19, 2009

(54) METHOD FOR PREPARING PYRROLOTRIAZINE COMPOUNDS VIA IN SITU AMINATION OF PYRROLES

(75) Inventors: Apurba Bhattacharya, Hyderabad (IN); Nitinchandra Patel, Gujarat (IN); John Anthony Grosso, Princeton Junction, NJ (US); Luca Parlanti, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 86 days.

(21) Appl. No.: 11/396,888

(22) Filed: Apr. 3, 2006

(65) Prior Publication Data

US 2006/0229449 A1 Oct. 12, 2006

Related U.S. Application Data

(60) Provisional application No. 60/668,765, filed on Apr. 6, 2005.

(51) Int. Cl.
*C07D 487/04* (2006.01)
*C07D 207/30* (2006.01)
*C07D 207/50* (2006.01)
(52) U.S. Cl. .................. 544/183; 548/530; 548/557
(58) Field of Classification Search .......... 544/183; 548/530, 557
See application file for complete search history.

(56) References Cited

U.S. PATENT DOCUMENTS 6,670,357 B2 12/2003 Leftheris et al.

FOREIGN PATENT DOCUMENTS

| WO | WO 00/71129 | 11/2000 |
|----|----|----|
| WO | WO 03/042172 | 5/2003 |
| WO | WO 03/090912 | 11/2003 |
| WO | WO 03/091229 | 11/2003 |
| WO | WO 2004/009601 | 1/2004 |
| WO | WO 2004/009784 | 1/2004 |
| WO | WO 2004/013145 | 2/2004 |

OTHER PUBLICATIONS

U.S. Appl. No. 60/584,382, filed Jun. 30, 2004, Shi, et al.
Greene, T. W. et al., "Protective Groups in Organic Synthesis", Wiley, NY, 3rd Edition, Table of Content, (1999),.

*Primary Examiner*—Venkataraman Balasubramanian
(74) *Attorney, Agent, or Firm*—Laurelee A. Duncan

(57) ABSTRACT

A method for aminating pyrrole derivatives via in situ generated chloramines and for preparing pyrrolotriazine compounds having the formula III,

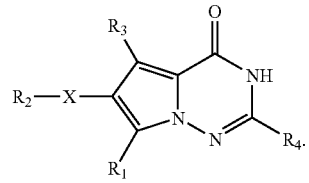

14 Claims, No Drawings

1

METHOD FOR PREPARING PYRROLOTRIAZINE COMPOUNDS VIA IN SITU AMINATION OF PYRROLES

RELATED APPLICATION

This application claims priority benefit under Title 35 § 119(e) of U.S. Provisional Application No. 60/668,765, filed on Apr. 6, 2005, the contents of which are herein incorporated by reference.

FIELD OF THE INVENTION

The invention relates to methods for preparing pyrrolotriazine compounds useful as components or precursors in the synthesis of pharmaceutical compounds having utility as anti-cancer agents and kinase inhibitors. The invention also includes an efficient method of aminating pyrrole compounds useful in the synthesis of pyrrolotriazines and other N-aminated heterocyclic compounds.

BACKGROUND OF THE INVENTION

Pyrrolotriazine-containing compounds have been found to be useful as anti-cancer agents as well as kinase inhibitors. See, e.g., WO 00/71129, WO 03/042172, WO 04/013145, WO 04/009784, WO 04/009601, WO 03/090912, WO 03/091229, U.S. Pat. No. 6,670,357, and U.S. patent application Ser. No. 60/584382, filed Jun. 30, 2004, which are commonly assigned to Bristol-Myers Squibb Co. The entire disclosure of each of the foregoing patent applications, patents, and publications is incorporated herein by reference.

SUMMARY OF THE INVENTION

This invention is directed to various methods for preparing pyrrolotriazine compounds as recited in the claims appended hereto. A pyrrolotriazine compound has the following formula III,

III wherein:
$R_1$ and $R_3$ are each independently hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$;
X is $-O-$, $-OC(=O)-$, $-S-$, $-S(=O)-$, $-S(=O)_2-$, $-C(=O)-$, $-C(=O)O-$, $-NR_d-$, $-NR_dC(=O)-$, $-C(=O)NR_d-$, $-NR_dC(=O)NR_d-$, $-NR_dC(=O)O-$, $-OC(=O)NR_d-$, $-NR_dS$ $(=O)_2-$, $-NR_dS(=O)_2NR_d-$, $-S(=O)_2NR_d-$, halogen, nitro, cyano, or a bond;
$R_2$ is selected from:
a) hydrogen, provided that $R_2$ is not hydrogen if X is $-S(=O)-$, $-SO_2-$, $-OC(=O)-$, $-OC(=O)NR_d-$, or $-S(=O)_2NR_d-$;
b) alkyl or substituted alkyl, alkenyl or substituted alkenyl, and alkynyl or substituted alkynyl, cycloalkyl or substituted cycloalkyl, cycloalkenyl or substituted cycloalkenyl;
c) heterocycle or substituted heterocycle, aryl or substituted aryl; and
d) $R_2$ is absent if X is halogen, nitro, or cyano;
$R_1$ and $R_2$ together may optionally form a 3-7 membered optionally substituted carbocyclic ring or 3-7 membered optionally substituted heterocyclic ring;
$R_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, aryl or substituted aryl, or heterocycle or substituted heterocycle;
$R_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;
$R_b$, $R_c$ and $R_d$ are independently hydrogen, alkyl or substituted alkyl, cycloalkyl or substituted cycloalkyl, heterocycle or substituted heterocycle, or aryl or substituted aryl, or said $R_b$ and $R_c$ together with the N to which they are bonded optionally form a heterocycle or substituted heterocycle;
$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl.

This invention is also directed to a method of aminating pyrrole derivatives useful in the synthesis of pyrrolotriazines and other N-aminated heterocyclic compounds.

DETAILED DESCRIPTION OF THE INVENTION

Abbreviation

Definition

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $Cl_3$), cyano, nitro, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle; and $R_e$ is alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, inorpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The terms "halogen" or "halo" refer to chlorine (Cl), bromine (Br), fluorine (F) or iodine (I).

The tern "Group I or Group II metal" refers to metal atoms in the first and second columns to the left of the Periodic Table of Elements. Exemplary metal elements include, but are not limited to, lithium (Li), sodium (Na), potassium (K), magnesium (Mg), and calcium (Ca).

The tern "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

Unless otherwise indicated, any heteroatom with unsatisfied valences is assumed to have hydrogen atoms sufficient to satisfy the valences.

The compounds of present invention may form salts which are also within the scope of this invention. Reference to compounds of the formula I through V herein is understood to include reference to salts thereof, unless otherwise indicated. The term "salt(s)", as employed herein, denotes acidic and/or basic salts formed with inorganic and/or organic acids and bases. In addition, when a compound contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds may be formed, for example, by reacting those compounds with an amount of acid or base, such as an equivalent amount, in a medium such as one in which the salt precipitates or in an aqueous medium followed by lyophilization.

The compounds of present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of present invention which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The tern "prodrug" as employed herein denotes a compound that, upon administration to a subject, undergoes chemical conversion by metabolic or chemical processes to yield compounds of the formula I through III, or a salt and/or solvate thereof. Solvates of the compounds of formula I through III include, for example, hydrates.

Compounds of the formula I through III, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

Methods of Preparation

The methods for preparing pyrrolotriazine compounds are illustrated in the following schemes. Solvents, temperatures, pressures, and other reaction conditions may readily be selected by one of ordinary skill in the art. Starting materials are commercially available or readily prepared by one of ordinary skill in the art.

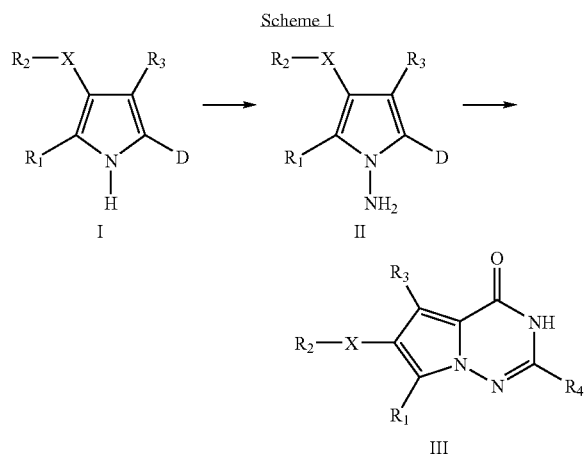

Scheme 1

A pyrrolotriazine of formula III can be prepared according to Scheme 1, wherein $R_1$, X, $R_2$, $R_3$, and $R_4$ are as defined above, and D is —C(=O)OR$_p$ in which R$_p$ is H, $C_1$-$C_6$ alkyl, or aryl, and preferably R$_p$ is Me or Et. An aminopyrrole of formula II can be synthesized by reacting a pyrrole of formula I with a chloramine generated in situ, in a two-phase solvent system (i.e., organic-aqueous), such as MTBE-$H_2O$. Any aqueous immiscible organic solvents can be used as the organic layer, for example, diethyl ether, tetrahydrofuran (THF), toluene, methylene chloride, and methyl tert-butyl ether (MTBE). The preferred organic solvent are MTBE and THF, and the most preferred is MTBE.

Cyclization of compound II with an amide of formula $R_4C$(=O)$NH_2$, preferably in the presence of an acid, forms the compound of formula III. The acid used in the cyclization step includes organic aliphatic/aromatic acid (e.g., acetic acid and trifluoroacetic acid) or resin supported acids (e.g., Amberlite I-120H). Preferred acids are phosphoric acid and acetic acid.

FIG. 1 describes the process of aminating pyrroles using in situ generated chloramines, in which Q represents a phase transfer catalyst. The pyrrole of formula I is deprotonated in the interphase by an aqueous base. Suitable bases include metal hydroxides, for example, Group 1/Group 2 metals such as Na, K, Mg, Ca, etc. Preferred bases are aqueous NaOH and aqueous KOH, and the most preferred is NaOH.

This deprotonation process is mediated by a phase transfer catalyst. Suitable phase transfer catalysts include organic ammonium compounds (e.g., poly alkyl/aryl ammonium halides or ammonium hydrogen sulfates); quaternary phosphonium compounds (e.g., poly alkyl/aryl phosphonium halides); quaternary pyridinium compounds (e.g., poly alkyl/aryl pyridinium halides); sulfonium compounds (e.g., poly alkyl/aryl sulfonium halides); surfactant like phase transfer catalysts (e.g., Triton-X 405, 18-Crown-6, etc.) such as Aliquat-336. Preferred catalysts are Aliquat-336 and cetyltrimethylammonium bromide, and most preferred is Aliquat-336.

Chloramine ($NH_2Cl$) is produced by oxidation of ammonia ($NH_3$) with a hypohalite, such as sodium or potassium hypochlorite (NaOCl/KOCl), sodium or potassium hypobromite (NaOBr/KOBr), and sodium or potassium hypoiodite (NaOI/KOI); or an equivalent thereof, for example, $Cl_2$+NaOH/KOH; $Br_2$+NaOH/KOH; and $I_2$+NaOH/KOH. Alternatively, the oxidation can be achieved using halogen in the aqueous layer, for example chlorine in the water.

Chloramine ($NH_2Cl$) is then transported from aqueous layer to organic layer; this process is mediated by the phase transfer catalyst present in the medium. The deprotonated pyrrole reacts with chloramine ($NH_2Cl$) in the interphase aided by phase transfer catalyst such as Aliquat-336 producing the N-aminated pyrrole. The product being organic soluble is transported to organic layer. This process is continued till all the starting material is consumed and converted to the N-aminated pyrrole product.

Other reagents that may help the reaction include an inorganic ammonium salts, Such as ammonium chloride and ammonium bromide. Preferred salt is ammonium chloride.

FIG. 1.

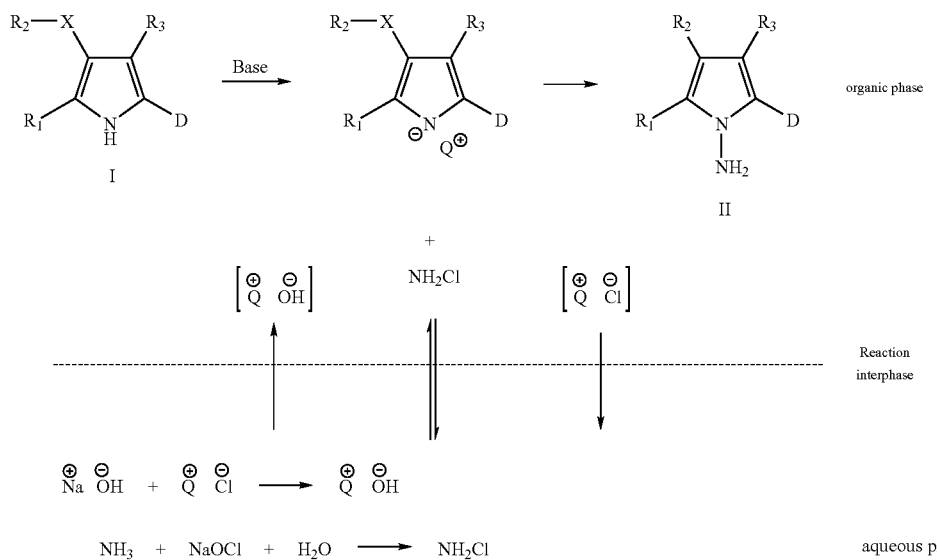

At the end of the process, the organic layer could be separated from the process; then the vessel could be recharged with some fresh organic layer (e.g., Methyl tert-butyl ether), ammonia, sodium hypochlorite, sodium hydroxide and pyrrole to start the N-amination reaction.

EXAMPLES

Example 1

Preparation of Compound 2:

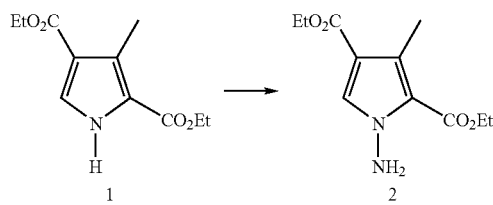

Compound 1 (2.00 g[1], 10.7 mmol) was dissolved in MTBE (methyl t-butyl ether) (24 mL). Ammonium chloride (2.89 g, 54.0 mmol), Aliquat-336 (0.12 g, 0.3 mmol), aqueous sodium hydroxide solution (28%, 25.6 mL, 181.7 mmol), and aqueous ammonium hydroxide solution (28%, 8.3 mL, 59.5 mmol) were added sequentially to the above solution while stirring. An aqueous sodium hypochlorite solution (9%, 58.8 mL, 88.8 mmol) was then added over 20 minutes. The reaction was stirred for four hours at room temperature. The phases were split. The organic layer was washed with aqueous sodium thiosulfate solution (34.5%, 40 mL) and the phases were split. The organic layer was distilled to a volume of about 2 mL and the crude was carried forward to the next step without further purification. $^1$H NMR (400 MHz, CDCl$_3$) δ 7.30 (s, 1H), 4.75 (br s, 2H), 4.28 (q, J) 7.1 Hz, 2H), 4.20 (q, J) 7.1 Hz, 2H), 3.83 (s, 3H), 1.32 (t, J) 7.1 Hz, 3H), 1.27 (t, J) 7.1 Hz, 3H). $^{13}$C NMR (100 MHz, CDCl$_3$) δ 162.9, 161.7, 151.8, 130.3, 113.3, 105.8, 63.3, 61.0, 60.3, 14.7, 14.7. MS (ESI) m/z 257.0 (M+H), calcd for C$_{11}$H$_{16}$N$_2$O$_5$ 256.1.

Note: [1.] 2.41 g of 83% pure compound 1 was used.

Example 2

Preparation of Compound 3:

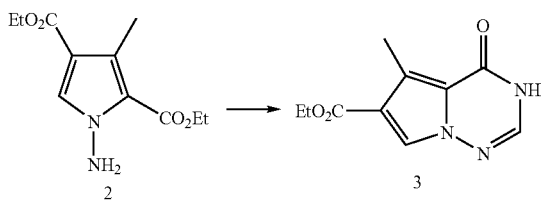

The above crude was treated with formamide (21.67 mL, 534.9 mmol, 50 equiv) and phosphoric acid (85%, 0.17 g, 44.9 mmol) at 40° C. The reaction was gradually heated to and stirred at 130° C. for 30 hours, and then was cooled to 60-75° C. Water (26 mL) was added over 30 minutes for crystallization. The mixture was further cooled to room temperature and stirred for 2 hours. The crystals were filtered, washed sequentially with water (24 mL) and hexane (20 mL), and dried at 50° C. under vacuum[2] to give compound 3 (1.63 g). $^1$H NMR (400 MHz, DMSO-D6) δ 7.87 (s, 1H), 7.84 (br s, 1H), 4.24 (q, J=7.1 Hz, 2H), 3.38 (br s 1H), 2.60 (s, 3H), 1.30 (t, J=7.1 Hz, 3H). $^{13}$C NMR (100 MHz, DMSO-D6) δ 163.3, 154.9, 139.9, 123.0, 117.7, 114.0, 59.4, 14.3, 11.0.

Note: [2.] Compound 3 was dried in a vacuum oven with a slow stream of nitrogen supplied.

What is claimed is:

1. A method for preparing a compound of formula III,

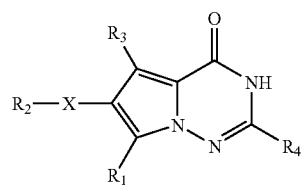

wherein:

R$_1$ and R$_3$ are each independently hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_e$, NR$_b$S(=O)$_2$R$_e$,NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$;

X is —O—, —OC(=O)—, —S—, —S(=O)—, —S(=O)$_2$—, —C(=O)—, —C(=O)O—, —NR$_d$—, —NR$_d$C(=O)—, —C(=O)NR$_d$—, —NR$_d$C(=O)NR$_d$—, —NR$_d$C(=O)O—, —OC(=O)NR$_d$—, —NR$_d$S(=O)$_2$—, —NR$_d$S(=O)$_2$NR$_d$—, —S(=O)$_2$NR$_d$—,halogen, nitro, cyano, or a bond;

R$_2$ is selected from:
a) hydrogen, provided that R$_2$ is not hydrogen if X is —S(=O)—, —SO$_2$—,—OC(=O)—, —OC(=O)NR$_d$—, or —S(=O)$_2$NR$_d$—;
b) alkyl or substituted alkyl, alkenyl or substituted alkenyl, and alkynyl or substituted alkynyl, cycloalkyl or substituted cycloalkyl, cycloalkenyl or substituted cycloalkenyl;
c) heterocycle or substituted heterocycle, aryl or substituted aryl; and
d) R$_2$ is absent if X is halogen, nitro, or cyano;

R$_1$ and R$_2$ together may optionally form a 3-7 membered optionally substituted carbocyclic ring or 3-7 membered optionally substituted heterocyclic ring;

R$_4$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, aryl or substituted aryl, or heterocycle, or substituted heterocycle;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl; cycloalkyl or substituted cycloalkyl, heterocycle or substituted heterocycle, or aryl or substituted aryl, or said $R_b$ and $R_c$ together with N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

comprising:

reacting a compound of formula I,

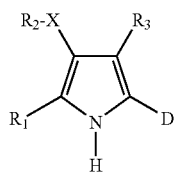

I wherein:

D is $C(=O)OR_e$, or $C(=O)NR_bR_c$;

with chloramine ($NH_2CL$) generated in situ, in the presence of aqueous base, phase transfer catalyst, wherein said phase transfer catalyst is Aliquat® 336 or cetyltrimethylammonium bromide, and optionally ammonium halide, and in a two-phase solvent system, to form a compound of formula II,

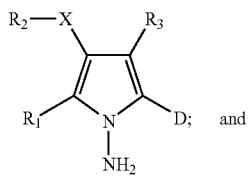

II and reacting the compound of formula II with an amide of formula $R_4C(=O)NH_2$;

in the presence of acid, to form the compound of formula III.

2. The method of claim 1, wherein $R_4$ is H and $R_e$ is Me or Et.

3. The method of claim 1, wherein said acid is phosphoric acid, acetic acid, or a mixture thereof.

4. The method of claim 1, wherein X is —C(=O)O—, $R_2$ is Et, $R_3$ is Me, $R_1$ is H, $R_4$ is H and D is —C(=O)OEt.

5. The method of claim 1, wherein said chloroamine is generated by contacting ammonia ($NH_3$) or ammonia hydroxide ($NH_3.H_2O$) with an oxidizing reagent.

6. The method of claim 5, wherein said oxidizing reagent is selected from the group consisting of NaOCl, KOCl, NaOBr, KOBr, NaOI, KOI, $Cl_2$, $Br_2$, and $I_2$, and in which said $Cl_2$, $Br_2$, and $I_2$ may optionally mix with water or an aqueous base.

7. The method of claim 6, wherein said oxidizing reagent is NaOCl.

8. The method of claim 1, wherein said aqueous base is Group 1 or Group 2 metal hydroxides.

9. The method of claim 1, wherein said aqueous base is sodium hydroxide or potassium hydroxide.

10. The method of claim 1, wherein said ammonium halide is present.

11. The method of claim 10, wherein said ammonium halide is ammonium chloride or bromide.

12. The method of claim 1, wherein the two-phase solvent system consists of water and aqueous immiscible organic solvent.

13. The method of claim 12, wherein said aqueous immiscible organic solvent is methyl tert-butyl ether, diethyl ether, tetrahydrofuran, toluene, methylene chloride, or a mixture thereof.

14. The method of claim 13, wherein said aqueous immiscible organic solvent is methyl tert-butyl ether, tetrahydrofuran, or a mixture thereof.

* * * * *

UNITED STATES PATENT AND TRADEMARK OFFICE
CERTIFICATE OF CORRECTION

| | | |
|---|---|---|
| PATENT NO. | : 7,534,882 B2 | Page 1 of 1 |
| APPLICATION NO. | : 11/396888 | |
| DATED | : May 19, 2009 | |
| INVENTOR(S) | : Apurba Bhattacharya et al. | |

It is certified that error appears in the above-identified patent and that said Letters Patent is hereby corrected as shown below:

In the Claims:

Claim 1:

Column 10, line 29, change "$NR_bR_e$, $NR_bS(=O)_2R_e$,$NR_bP(=O)_2R_e$," to -- $NR_bR_c$, $NR_bS(=O)_2R_e$, $NR_bP(=O)_2Re$, --.

Column 10, lines 38 and 39, change "—$S(=O)_2NR_d$—,halogen," to -- —$S(=O)_2NR_d$—, halogen, --.

Column 10, lines 58 and 59, change "heterocycle," to -- heterocycle --.

Column 10, line 66, change "alkyl;" to -- alkyl, --.

Column 11, line 1, change "$R_b$and" to -- $R_b$ and --.

Column 11, line 1, change "N" to -- the N --.

Column 11, lines 13 to 19, change " 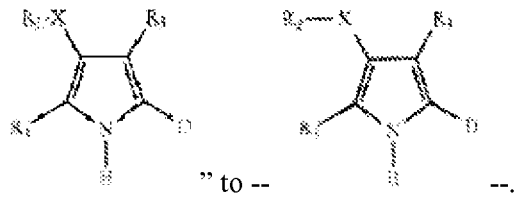 " to -- --.

Column 11, line 24, change "($NH_2CL$)" to -- ($NH_2Cl$) --.

Column 12, line 3, change "of acid," to -- of an acid, --.

Claim 6:

Column 12, line 15, change "NaOCl, KOCl," to -- NaOCl, KOCl, --.

Signed and Sealed this
Tenth Day of April, 2012

David J. Kappos
*Director of the United States Patent and Trademark Office*